United States Patent [19]

Biehl et al.

[11] Patent Number: 4,775,795
[45] Date of Patent: Oct. 4, 1988

[54] METHOD AND APPARATUS FOR DETECTING VERY SMALL CONCENTRATIONS OF GASES IN A GAS MIXTURE

[75] Inventors: Karl-Ernst Biehl, Hanau; Egon Tyssen, Alzenau; Conrad G. von Roedern, Kiel, all of Fed. Rep. of Germany

[73] Assignee: Honeywell-Elac-Nautik GmbH, Fed. Rep. of Germany

[21] Appl. No.: 13,983

[22] Filed: Feb. 12, 1987

[30] Foreign Application Priority Data

Feb. 15, 1986 [DE] Fed. Rep. of Germany ....... 3604893

[51] Int. Cl.⁴ .............................................. G01T 1/10
[52] U.S. Cl. .................................................... 250/379
[58] Field of Search ................... 250/374, 379, 385 R

[56] References Cited

U.S. PATENT DOCUMENTS 4,238,678 12/1980 Castleman et al. ............. 250/385 X
4,362,941 12/1982 Castleman et al. ............. 250/385 X

*Primary Examiner*—Gene Wan
*Attorney, Agent, or Firm*—Mitchell J. Halista; Albin Medved

[57] ABSTRACT

A method for detecting very small concentrations of gases in gas mixtures passed as a gas stream through a measuring cell having a chamber through which the gas stream flows through, a drift zone provided between an inlet and an outlet of the chamber, a gas stream ionizing radiation source located at the inlet of the drift zone, a collector electrode located at the outlet of the drift zone, a grid consisting of two groups of parallel wires located in the drift zone current adjacent grid wires are supplied with different electrical voltages and whereat an AC voltage of adjustable frequency is fed to the two groups of grid wires, and a measuring apparatus for detecting the collector current, including the steps of inducing the movement of the ions through the drift zone by means of a ventilator which generates a controlled gas flow to the collector electrode, periodically changing the frequency of the AC voltage applied to the groups of grid wires either continuously or stepwise, simultaneously measuring the collector current dependent on the grid frequency, digitizing and storing the measured collector current in a memory as a function of the frequency, storing in a further memory a table of collector current/frequency curves for different gases, comparing the measured curves with the stored curves and, if a measured curve is identical with one of the stored curves, producing an indication signal characterizing the gas corresponding to the particular stored curve. An apparatus for measuring a gas concentration is provided using this method.

18 Claims, 4 Drawing Sheets

METHOD AND APPARATUS FOR DETECTING VERY SMALL CONCENTRATIONS OF GASES IN A GAS MIXTURE

BACKGROUND OF THE INVENTION

1. Field of the Invention

This invention relates to gas detectors. More specifically, the present invention is directed to gas detectors for detecting very small gas concentrations in a gas mixture.

2. Description of the Prior Art

The detection of very small concentrations of gases or vapors in air or other gas mixtures by using an ionization measuring cell is known in principle from U.S. Pat. No. 4,119,851. In that well-known method of ion-mobility spectroscopy, ions move under the influence of an electrostatic field through a drift zone. A voltage in the order of 2 kV is provided between the radiation source and a collector electrode for generating this eletrical field. Since light ions move faster than heavy ions, the ions started at a predetermined time reach the collector electrode after different times-of-flight depending on their respective molecular weight. Short current pulses are generated when such an ion package reaches the collector electrode. The time position of such a current pulse within a time-of-flight spectrum depends on the mass of the respective ions and therewith permits sorting the ions dependent on their mass. The intensity of the current pulse is a measure for the number of ions of a predetermined mass within the ion package which started at a predetermined time. For detecting particular ions therefor a time-of-flight analysis of the ion current is required. Furthermore, the drift zone must have a sufficient length in order that the time distance between the arrival of ions of different mass at the collector electrode permits a separation of the individual current pulses and thereby permits the detection cf individual groups of ions. Such a prior art device requires a high voltage supply, a time-of-flight analysis and a relatively long drift zone which significantly increases the cost and size of the device. Accordingly, it would be desirable to provide a method and apparatus for detecting gas concentrations which avoids those limitations of the prior art to produce a compact, easily mobile, reliable and relatively inexpensive device.

SUMMARY OF THE INVENTION

An object of the present invention is to provide an improved method and apparatus for detecting very small concentrations of gases in a gas mixture.

In accomplishing this and other objects, there has been provided, in accordance with the present invention, a method for detecting very small concentrations of gases in a gas stream passed through a measuring cell having the chamber through which a gas stream flows through, a drift zone provided between a gas stream inlet and an outlet of the chamber, an ionizing radiation source located at the inlet of the drift zone, a collector electrode located at the outlet of the drift zone, a grid consisting of two groups of parallel wires located in the drift zone including the steps of inducing the movement of the ions through the drift zone by means of a ventilator which produces a controlled gas flow to the collector electrode, supplying adjacent grid wires with different AC voltages of adjustable frequency, periodically changing the frequency of the AC voltage applied to the groups of grid wires either continuously or stepwise, simultaneously measuring the collector current dependent on the grid frequency, digitizing and storing the measured collector current in a memory as a function of the frequency, storing in a further memory a table of collector current/frequency curves for different gases, comparing the measured curves with the stored curves and, if a measured curve is identical with one of the stored curves, producing an indication signal characterizing the gas corresponding to the particular stored curve. An apparatus for measuring a gas concentration within a gas stream comprising a measuring chamber cell through which the gas stream flows, a drift zone provided between an inlet and a gas stream outlet of said chamber, an ionizing radiation source located at the inlet of said drift zone, a collector electrode located at the outlet of said drift zone, a grid of two groups of parallel wires located in said drift zone, a ventilator means for producing a controlled gas flow to said collector electrode and a measuring apparatus for detecting a collector current from said collector electrode including means for supplying adjacent grid wires in said grid with different AC voltages of adjustable frequency, means for periodically changing the frequency of the AC voltage applied to said grid wires, means for concurrently measuring the collector current dependent on the grid voltage frequency and means for comparing the measured collector current with collector/frequency curves for different gases.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

In distinction from the prior art, the movement of the ions in the present invention is not accomplished by means of an electrostatic field, but rather the carrier gas mixture is moved through the drift zone by means of a ventilator. According to the invention, the flow velocity of the gas mixture preferably is maintained constant. The electrical potential at the collector electrode only is used for absorbing the arriving ion packages. No high voltage is required between the collector electrode and the ion source. Furthermore, the time-of-flight analysis of the arriving ion packages is omitted which in the prior art is required and is complicated and requires a relatively long drift zone. Instead, a measurement of the collector current dependent on the frequency of an AC voltage applied to a grid of two groups of parallel wires located between the ion source and the collector electrode is provided. The detector thereby can be designed to be shorter and more compact. The novel method according to the invention is based on the use of the frequency of the AC voltage fed to the grid wires to determine which portion of ions of a predetermined mass is permitted to move through the grid and thereby to reach the collector electrode. If the frequency is modulated or changed over a predetermined range of frequencies, either stepwise or continuously, different types of ions are permitted to flow through the grid dependent on the particular frequency. Dependent on whether or not ions of a first or a second gas are present in the gas mixture, a collector current pulse associated with a particular frequency and thereby to a particular type of gas will be present or not. When modulating the frequency over the entire range, the generated collector current curve is compared with a stored collector current curve. By this comparison it can be determined which type of gas is present in the gas mixture under measurement. This comparison is provided automatically and in digital manner by means of a microprocessor so that a high reliability of the detection method is achieved.

Figure 3:
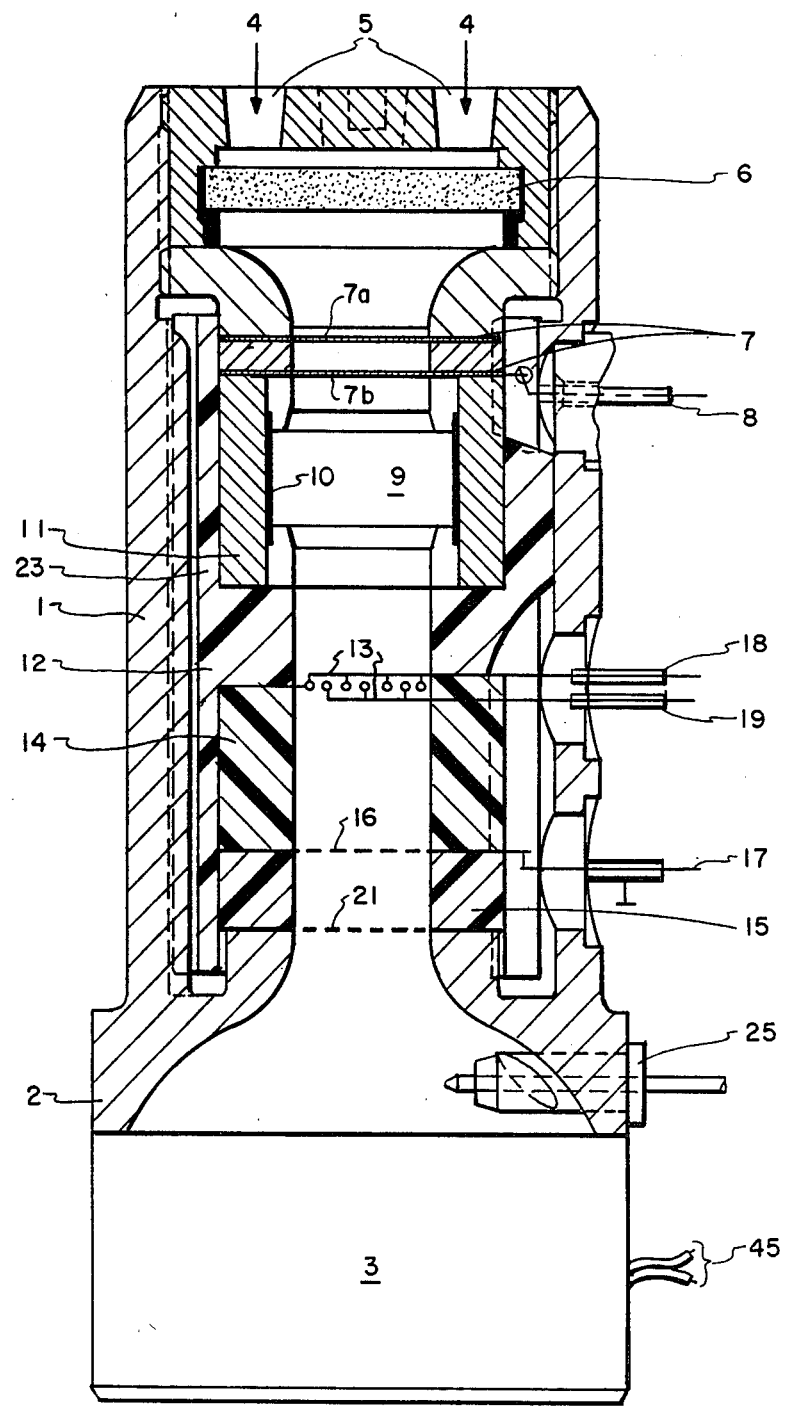
FIG. 3 is a cross-sectional illustration of a measuring cell embodying an example of the present invention.

A measuring cell embodying an example of the present invention is shown in FIG. 3 and consists of an essentially tube-like metal housing 1 with a flange 2 sealed to its outlet side. The flange 2 carries a ventilator device, e.g., a motor driven fan 3, by means of which an air stream is sucked through inlet openings 5 provided at the inlet side of the tube 1 with this air stream containing the small concentration of trace gases which have to be detected. The gas stream flows through a mechanical filter 6 and then moves to a mesh-like flow divider 7 which makes the inlet flow uniform and generates an essentially laminar gas stream. Flow divider 7 consists of two meshes 7a and 7b, located one behind the other, which are connected electrically to each other. Both meshes together are electrically connected to the metal housing 1 and are also connected to an electrical terminal 8 which is used as the source or emitter terminal. A subsequent flow channel 9 of the housing in the flow direction is surrounded by a ring shaped foil 10 which is coated with a radioactive material, e.g., Americium 241, used as radiation source for ionizing the gas stream. The foil 10 is carried by a metal bushing 11 which is electrically connected to terminal 8, flow divider 7 and housing 1. Herewith focusing of ions of desired polarity within the gas flow is accomplished together with isolation against external influences. A grid 13 follows in the flow path after bushing 11 and is electrically isolated from the bushing 11 by means of an intermediate piece 12 made of plastic. Grid 13 is supported by a ceramic bushing 14 and consists of two groups of alternate parallel wires which are electrically isolated from each other. Consequently, two groups of parallel wires are provided so that adjacent grid wires can be supplied with different electrical voltage whereby an electrical AC field is generated between the two groups of electrical wires.

In the subsequent flow path, a collector electrode 16 in the form of a mesh is located and is separated electrically from grid 13 by means of an insulating bushing 14. Collector electrode 16 is located at the outlet of the drift zone and is connected to collector terminal 17. The two groups of grid wires 13 are connected to grid electrical terminals 18 and 19. The collector electrode 16 is supported by an insulating bushing 15, which on its opposite side carries a further mesh-like flow divider 21. This flow divider 21 accomplishes an almost laminar gas flow on the outlet side or the drift zone, i.e., before the flow reasches the ventilator 3. This ventilator generates by means of a speed control circuit a uniform gas stream through the housing 1. Bushings 14 and 15, isolating ring 12 and metal bushing 11 are at least partially surrounded by a plastic sleeve 23 which includes the distance piece 12 and isolates those parts from the outer metal tube 11. The collector electrode 16 is maintained at reference potential by means of a voltage applied to the terminal 17. The flow divider 21 at the outlet side is connected to metal housing 1 in order to electrically screen collector electrode 16.

The following explanation of the operation of the cell shown in FIG. 3 assumes that the gas stream entering the cell at the suction side 4 is an air stream which comprises only a single trace gas. This gas mixture after a smoothing of iots flow within flow divider 7 enters the space 9 which is surrounded by the radiation generating foil 10. In this space 9, the air molecules as well as the trace gas molecules are ionized partially directly and partially indirectly. The air molecules have an essentially smaller mass than the trace gas molecules. The gas stream then moves to grid 13, whose wires are connected alternately to different electrical voltages. The two groups of grid wires are supplied with square wave voltages via terminals 18, 19 with these square wave voltages having the same frequency but being offset with respect to their phases by 180°. The average value of the electrical potential at grid 13 corresponds to the electrical potential at the location of the grid 13 which is generated by the electrical DC field extending between the collector electrode 16 and the radiation source 9,11. Between the individual grid wires 13 an electrical alternating field is effective in a direction transverse with respect to the flow direction of the gas stream. This electrical transverse field is used to deflect the ions out of their travel direction. This will be accomplished more easily if the mass of the ions is small and the frequency of the alternating field is low. Heavy ions, because of their mass and inertia, will not be deflected by the electrical AC field from their traveling path as easily as light ions.

If a static electrical field is present at the two grids 13, a part of the deflected ions will impinge on the grid wires 13, and the electrical charge of these ions will be removed via the grid wires 13. If, on the other hand, an alternating field of very high frequency is provided between the two groups of grid wires 13, neither light ions nor even heavy ions can follow the forces of this quickly changing AC field and therefore will not be deflected but rather will travel through the grid 13. The lighter the ionized molecules are and the lower the frequency is, the more ionized molecules will transmit their charge to grid 13 and thereafter will move electrically neutral with the gas flow in the direction to collector electrode 16. The number of ionized molecules arriving at collector 16 therefore depends on the one hand upon the mass of these molecules and on the other hand upon the frequency of the AC voltage fed to the two groups of wires of the grid 13. The measuring cell thereby uses the different ion mobility of air ions and gas ions as the critical value for distinguishing between them.

Besides the ventilator 3 effecting the gas stream flow, a second force urging the ions to move is formed by the electrical field between ion source 9, 10 and collector 16 which influences the speed of the ions. The strength of this field, however, in view of a low voltage, e.g., five volts, between source and collector means that this accelerating influence on the axial traveling velocity of the ions can be ignored. This field, however, generates a flow focusing transverse component between the metal housing 1 and the grid 13 and the metal housing 1 and the collector 16, respectively, which provides the required difusion rate for ions having an undesired polarity. Since, in distinction to the prior art measuring cell, no axial time-of-flight selection of the ions is provided, such small changes or fluctuations of the time-of-flight caused by the small electrical field do not essentially influence the measuring result. However, the omission of a high voltage generator is an essential advantage, in particular for a measuring cell used in a portable apparatus and with respect to its operation safety.

As mentioned above, at very high grid frequencies practically all ions will travel through the grid 13 without being deflected and will reach the collector 16. The collector current measured at such a high grid frequency therefore is a measure of the total number of all ions contained in the gas stream and thereby is a measure for the gas stream itself and its speed of flow. This collector current "$I_0$" measured at a very high grid frequency may be supplied as actual value to a speed control circuit for ventilator 3 in order to maintain a constant flow rate of the gas stream by controlling the speed of the ventilator 3.

Figure 1:
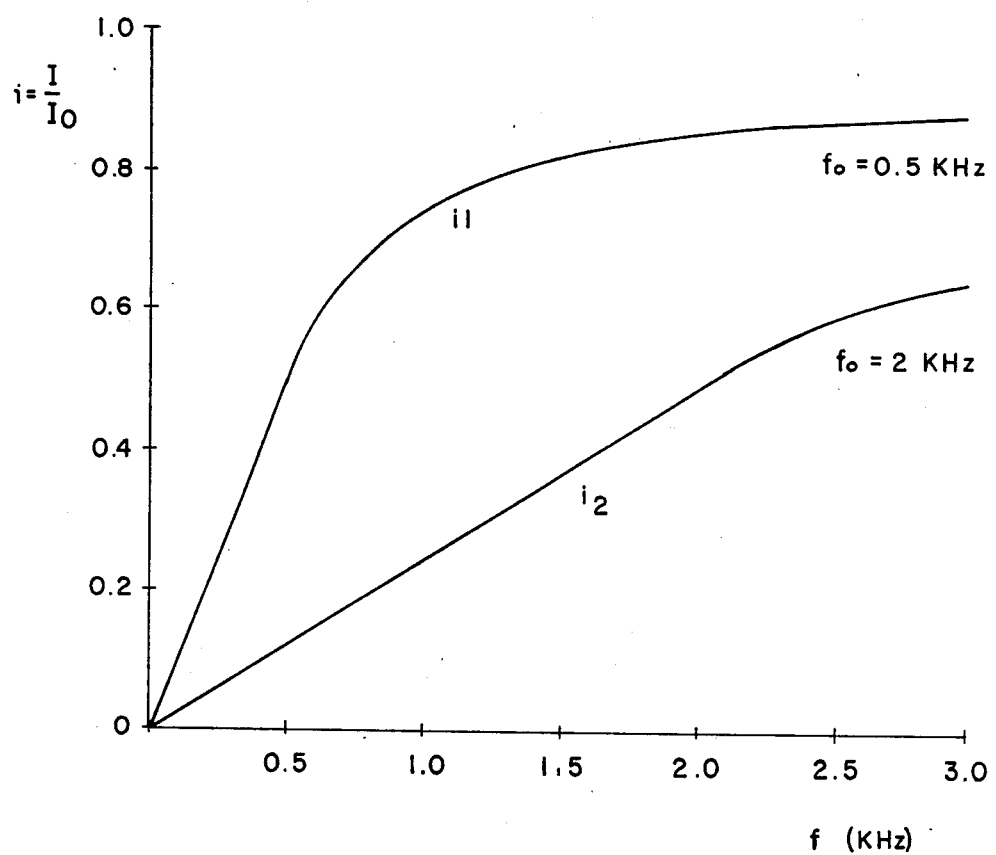
FIG. 1 is a graph showing the dependency of the standardized collector current "i=I/Io" dependent on the grid frequency "f" for two types of ions of different movability.

A further method for determining the flow rate of the gas stream provides measuring the traveling time of the ions between grid 13 and collector electrode 16. The physical distance between those electrodes is known. The flow rate can be calculated from this distance as well as the required traveling time. It is assumed in this method that ion view of the weak electrical longitudinal field between the grid 13 and the collector electrode 16 the flow rate of the gas stream will differ only very little, if any from the traveling velocity of the ions. A stepwise frequency change at the grid 13 is provided and the travel time effect is measured until this stepwise frequency change results in a corresponding stepwise change of the collector current. Since during a continuous gas analysis the grid frequency is changed cyclically it is possible within each cycle to provide such a stepwise change and therewith to measure the ion traveling time and therewith the flow velocity. This actual value of the flow rate is then applied to the speed controller for the ventilator 3. FIG. 1 shows the dependency of a standardized collector current "i" upon the frequency "f" for gases of different ion mobility. As a standardized collector current "i", the relation of the actual collector current "I" measured dependent upon the frequency to the maximum collector current "$I_o$" is shown in FIG. 1, whereat the maximum collector current as mentioned above was measured at very high grid frequencies. Curve "$i_2$" originates from a gas whose ions have about four times the ion mobility compared with the gas generating curve "$i_1$". The ion mobility can be represented as a frequency, namely as that frequency "$f_0$" at which the ion current reaches half of the maximum achievable value. With a constant gas flow through the measuring cell, "$f_0$" depends on the speed of the ions and the distance of the grid wires. Since this distance is constant, the frequency "$f_0$" is directly proportional to the ion mobility. For example, a grid was used whose parallel wires have a diameter of 0,08 mm and a distance of 0,4 mm. As can be seen from FIG. 1, the collector current "$i_1$" of the faster or more mobile ions ($f_0=2$ kHz). The reason for this fact is that at the grid 13 the more mobile ions can follow the electrical alternating field to high frequencies and can recombine. The large amount of the less mobile ions, however, at this frequency during one-half period of the grid AC voltage does not reach the adjacent wire of the grid and therefor travels further to the collector 16. At the collector 16, this ion is neutralized and generates a current pulse.

The two curves "$i_1$" and "$i_2$" show a typical curve of a standardized collector current "i" defendent on the frequency and the ion mobility. Because of these properties, the described measuring cell is suitable to distinguish different gases by reference to the curve of its collector current when dependent on the grid frequency. A group of such standardized collector current curves $i_1$, $i_2$ etc., each one dependent on the grid frequency, may be stored in a memory. Each of these curves is characteristic of one particular type of gas. An unknown gas mixture is tested by periodically modulating the frequency of the AC voltage fed to the grid wires either continuously or in small steps. At the same time the collector current or the standardized collector current is measured dependent on the actual grid frequency. This measuring value is digitized and as function of the actual frequency is stored in a second memory. By comparing the stored measuring curve with the previously stored curves characteristic of particular gases, it can be determined which trace gas is contained in the gas flow under measurement. Such a comparison of digitally stored data preferably is accomplished by means of a microprocessor which provides an indication signal characterizing a predetermined vapor or gas if the measured current/frequency curve corresponds to one of the stored curves. These curves preferably are stored digitally as a table of values.

In many cases it will not be necessary to modulate through the entire frequency range, but it might be sufficient to work with a group of preselected test frequencies. As a first step, the saturation value "$I_0$" of the collector current is determined at a very high frequency of, e.g., 15 kHz. From this saturation value a sufficient number of frequency-dependent current values at predetermined frequencies can be derived for the current/frequency curve of air and can be stored as reference values. Eventually these values can be verified by measuring the current at a few predetermined frequencies. For analyzing an unknown gas, these test frequencies are generated one after the other, and the collector current is measured and is digitized by means of an A/D converter. Either the values associated with the predetermined frequencies are stored or they are compared on-line directly with the stored values of the curve for air. In this manner curves typical for predetermined types of gas can be recognized and, in the case of a concentration exceeding a predetermined concentration limit, an alarm signal might be generated.

Figure 4:
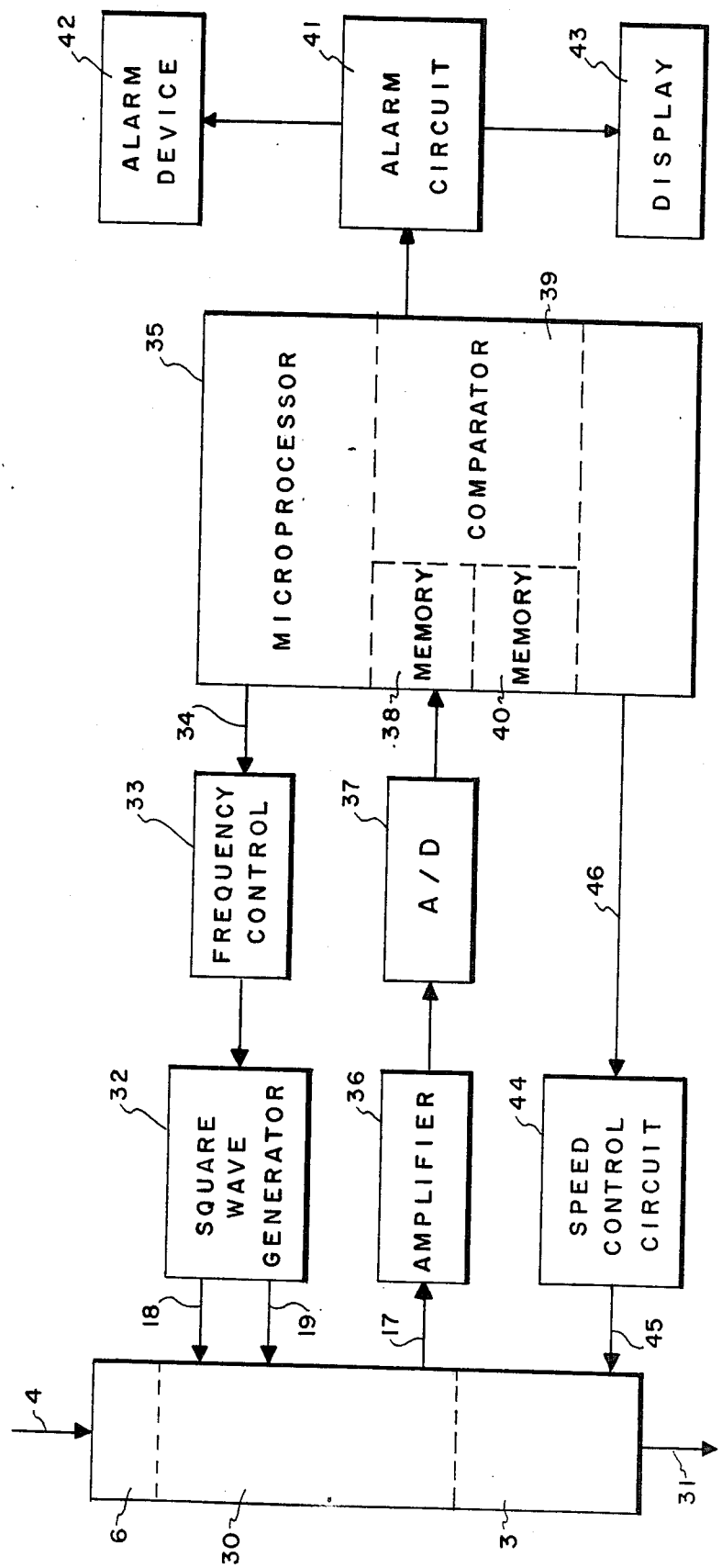
FIG. 4 shows a block diagram of a signal handling circuit connected to the output of the measuring cell shown in FIG. 3.

In the block diagram of FIG. 4 there is shown a gas inlet 4, filter 6, ventilator 8 and air outlet 31 as a block but internally has the design of the cell as shown in FIG. 3. A square wave generator 32 generates on lines 18 and 19 (see FIG. 3) AC signals of opposite phase relation for the two groups of the grid wires of the grid 13. The frequency of these square wave signals can be either continuously or stepwise changed by means of a frequency control circuit 33. This frequency control circuit 33 changes the frequency in accordance with an output signal on a frequency control line 34 of a microprocessor 35. The collector current on the line 17 is fed to an amplifier 36 and from the output of this amplifier to an analog-to-digital (A/D) converter 37. The digitized collector current signal is written into a memory 38 of the microcomputer 35 and by means of a digital comparator 39 is compared with several current/frequency curves which are stored in a further memory 40. Both curves preferably are stored in the form of data tables. If a particular, e.g., a dangerous type of gas or concentration of gas is recognized, an alarm circuit 41 is enabled and an acoustic or optical alarm device 42 is rendered active. The recognized type and/or concentration of the trace gas can be indicated on an optical indicator 43. In addition, a recorder might be connected to the alarm circuit 41 or immediately to an output of microcomputer 35.

At high flow rates within the measuring cell 30 more ions reach the collector 16 per unit of time than at low flow rates. In order to remove such influence of the flow rate on the collector current signal either a correction dependent on the flow rate is provided for the collector current signal or the flow rate is maintained constant. For measuring the flow rate a well-known flow sensor might be used. The flow rate is controlled by means of the speed of the ventilator 3. Instead of using a separate flow sensor the collector current itself might be used for generating a flow-dependent signal As mentioned above, the collector current "$I_0$" at a very high grid AC frequency is characterizing the flow rate. At such a high frequency of, e.g., 15 kHz, no ions impinge upon the grid 13, but all flow through the grid 13 to the collector 16 and there form the collector saturation current $I_0$. This current simultaneously is a measure for the flow rate and therefore, by means of a speed control circuit 44, can be used for controlling the speed of the ventilator 3. This can be achieved by changing the supply voltage for the ventilator 3 as supplied via line 45 or in case of a pulse or three-phase motor the frequency of the exciting voltage can be changed. A signal corresponding to the actual flow rate and the collector saturation current is supplied to the control circuit 44 from microcompouter 35 via line 46. This signal is generated by the microcomputer 35 by using the output signal of converter 37 which is associated with a very high grid frequency. As mentioned above, the flow rate of the gas stream alternatively can be determined by measuring the traveling time of a ion pulse between the grid 13 and the collector electrode 16.

As mentioned above, the distinction between trace gases and air molecules essentially is accomplished based on the essentially higher mass of ionized trace gas complexes. The electrical field provided between the source electrode and the collector electrode determines the polarity of the ions which have to be investigated. If clean air is fed to the measuring cell, the measuring values developed in this case may be used for calibrating the signal handling circuitry connected to the measuring cell. Any dependency of the collector current on humidity, which might be generated when trace gases are present in the form of competitive processes with negative influence on the formation of molecule complexes, can either be considered by using a humidity sensor, the output signal of which is supplied to the microcomputer 35 to generate a correction value corresponding to the absolute humidity. Another measure for avoiding influences of changing humidity is to maintain the humidity constant at the input of the measuring cell, e.g., by means of a dehumidifying apparatus or heating apparatus. In a similary manner, the influence of temperature changes onto the measuring result can be compensated, e.g., a temperature increase increases the ion mobility. If the output signal of a temperature sensor 25 is fed to the microcomputer 35, it can develop a corresponding correction signal for the collector current signal, i.e., for the slope of the stored reference curve.

Figure 2:
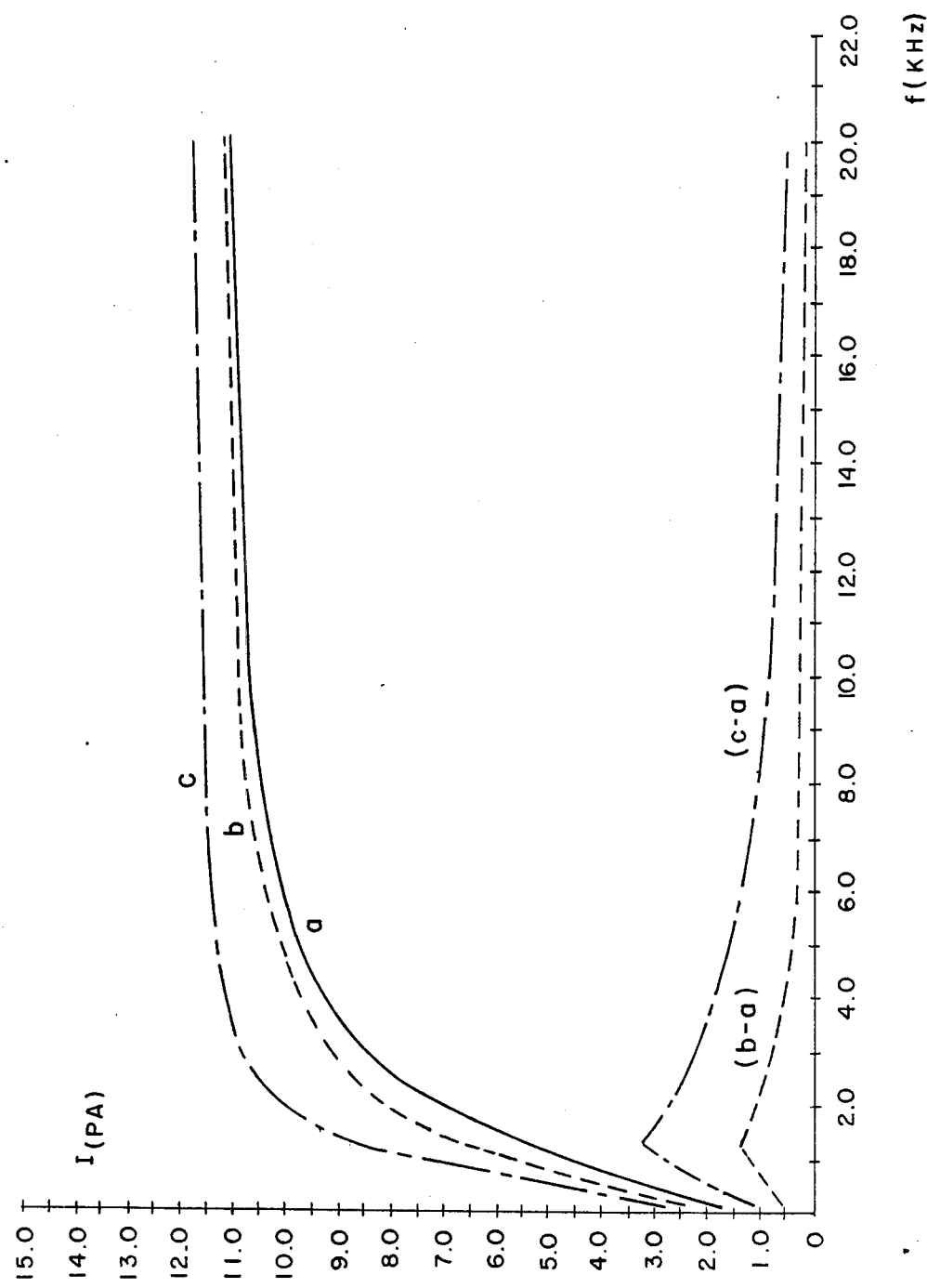
FIG. 2 is a graph showing the collector current "I" for filtered air and two air/gas mixtures of different concentration dependent on the grid frequency "f" together with the differential curves dependent on concentration and derived from the collector current curves.

With a method as described above and by the apparatus explained before, it is not only possible to recognize different types of trace gases but simultaneously the concentration of such trace gases can be determined. This will now be expxlained by reference to FIG. 2. FIG. 1 shows that the slope of the current/frequency curve in the linear raising range changes dependent on the ion mobility. By measuring the collector current at two predetermined test frequencies, the slope of the curve can be determined. FIG. 2 shows a curve "a" which is the current/frequency curve for filtered air at eleven percent relative humidity. Curve "b" shows a similary curve if 0,050 μg per liter of Sarine are added to the air with eleven percent relative humidity. Curve "c" shows again air with eleven percent relative humidity but in addition with 0,106 ug per liter of Sarine added. By using test frequencies of 312.5 Hz and 1.250 Hz for filtered air, a slope of 3.28 pA/kHz is shown. Curve "b" has a slope of 4.07 pA/kHz, and curve "c" has a slope of 5.18 pA/kHz. By determining the slope of the curve within the linear range between two predetermined test frequencies, the concentration of the trace gas can be determined by the microcomputer 35. Furthermore, as also shown in FIG. 2 the difference of the current values between filtered air and a curve associated with air containing a trace gas of different concentration can be calculated. These are curves "c−a" and "b−a". An alarm can be activated if at a predetermined frequency this differential value exceeds a predetermined level. In the shown example the differential curve "b−a" at a frequency of f=0.7 KHZ is below the value of 1.0 pA, whereat curve "c−a" at the same frequency is above 2.0 pA. Thus, by storing corresponding calibration curves not only a concentration exceeding a predetermined limit can be detected, but also the value of the concentration itself can be determined.

Accordingly, it may be seen that there has been provided, in accordance with the present invention, an improved method and apparatus for detecting very small concentrations of a gas in a gas mixture.

The embodiments of the present invention in which an exclusive property or priviliege is claimed are defined as follows:

1. A method for detecting very small concentrations of gases in a gas mixture passed as a gas stream through a measuring cell having
   a chamber through which gas stream flows,
   a drift zone provided between an inlet and an outlet of the chamber,
   a gas stream ionizing radiation source located at the inlet of the drift zone,
   a collector electrode located at the outlet of the drift zone,
   a grid consisting of two groups of parallel wires located in the drift zone, including the steps of inducing the movement of the ions through the drift zone by ventilation means which produces a controlled gas flow to the collector electrode, supplying adjacent grid wires with different AC voltages of adjustable frequency, periodically changing the frequency of the AC voltage applied to the groups of grid wires, simultaneously measuring the collector current dependent on the grid voltage frequency, digitizing and storing the measures collector current in a memory as a function of the frequency, storing in a further memory a table of collector current/frequency curves for different gases, comparing the measured curves with the stored curves and producing an indication signal characterizing the gas corresponding to the particular stored curve upon the detection of an identity between a measured curve and a stored curve.

2. A method as set forth in claim 1 and including the further step of maintaining the flow rate of the ions through the measuring cell constant by a speed control of the ventilator.

3. A method as set forth in claim 2, wherein the collector current is measured at a frequency far higher than the normal operating range of grid frequencies and is compared with a stored setpoint and a correction signal is derived from this comparison for controlling the speed of the ventilator.

4. A method as set forth in claim 2, and including the further steps of initiating during a measuring cycle a stepwise frequency change at the grid and the corresponding stepwise change of the collector current as delayed by the traveling time of the ions between the grid and the collector electrode is determined, and from this traveling time of the ions and the known physical distance between the grid and the collector electrode the flow rate of the gas stream is calculated.

5. A method as set forth in claim 1 wherein both groups of grid wires are excited with respective square wave signals having the same frequency but being offset with respect to their phase by 180° and that the average voltage of both groups of grid wires corresponds to the electrical potential at the location of the grid within the electrical field extending between the source electrode and the collector electrode.

6. A method as set forth in claim 1 wherein the value of the collector current measured at a higher frequency of the grid AC voltage is subtracted from the collector current value measured at a lower frequency of the grid AC voltage, and the slope of the collector current/frequency curve derived from this subtraction is compared with a stored concentration value associated with the tested gas.

7. A method as set forth in claim 1 wherein for determining the concentration of a detected gas the collector current value "a" of a clean gas is substrated from the collector current value "b" of a gas mixture comprising trace gases and that the differential value "b−a" is compared with a limit value associated with the same frequency.

8. An apparatus for measuring a gas concentration within a gas stream comprising a measuring chamber through which the gas stream flows, a drift zone provided between an inlet and an outlet of said chamber, a gas stream ionizing radiation source located at the inlet of said drift zone, a collector electrode located at the outlet of said drift zone, a grid of two groups of parallel wires located in said drift zone a ventilation means for producing a controlled gas flow to said collector electrode and a measuring apparatus for detecting a collector current from said collector electrode including means for supplying adjacent grid wires in said gird with different AC voltages of adjustable frequency, means for periodically changing the frequency of the AC voltage applied to said grid wires, means for concurrently measuring the collector current dependent on the grid voltage frequency, and means for comparing the measured collector current with collector/frequency curves for different gases.

9. An apparatus as set forth in claim 8 wherein said means for supplying includes a square wave-generator having two output square- wave signals displaced 180° with respect to each other with each of said output signals being applied to a respective group of said parallel wires.

10. An apparatus as set forth in claim 9 wherein said means for comparing includes a first memory and an A/D converter connecting said collector electrode to said memory to store store a table of collector current signals therein as a function of the frequency of the square-wave signals.

11. An apparatus as set forth in claim 9 wherein said means for supplying includes means for digitally controlling the frequency of said square-wave signals.

12. An apparatus as set forth in claim 10 wherein said means for comparing includes a second memory for storing a table of collector current/frequency curves for different gases and wherein said means for controlling includes means for comparing the table stored in said first memory with said table stored in said second memory to produce an indication of the gas being tested.

13. An apparatus as set forth in claim 9 wherein said means for supplying includes means for modulating the frequency of the square-wave signals according to a predetermined pattern.

14. An apparatus as set forth in claim 13 wherein said modulation pattern is continuous.

15. An apparatus as set forth in claim 13 wherein said modulation pattern is discontinuous.

16. An apparatus as set forth in claim 8 wherein a temperature sensor is provided in the gas stream and its output is connected to the microcomputer.

17. An apparatus as set forth in claim 8 wherein a mechanical filter is provided at an inlet of said measuring cell and a flow smoothing flow divider is provided within said cell consisting of two spaced apart meshes.

18. An apparatus as set forth in claim 17 wherein a mesh-like flow divider is provided between the drift zone and said ventilation means.

* * * * *